United States Patent
Betto et al.

[11] Patent Number: 5,961,476
[45] Date of Patent: Oct. 5, 1999

[54] WALK ASSISTING APPARATUS

[75] Inventors: Arimitsu Betto, Takasaki; Hideaki Torii, Kobe; Hideo Yano, Tokorozawa; Hidetugu Fujitani, Ibaragi-ken, all of Japan

[73] Assignee: Technology Research Association of Medical and Welfare Apparatus, Tokyo, Japan

[21] Appl. No.: 08/962,767

[22] Filed: Nov. 3, 1997

[30] Foreign Application Priority Data

Jul. 28, 1997 [JP] Japan .................................. 9-201120

[51] Int. Cl.⁶ ................................ A61F 5/01; A61F 2/60; A63B 22/08
[52] U.S. Cl. ................................. 602/16; 602/23; 623/31; 482/51
[58] Field of Search .............................. 623/31; 602/16, 602/23, 26, 24, 27; 482/51; 607/48, 49; 600/595

[56] References Cited

U.S. PATENT DOCUMENTS

| 2,690,176 | 9/1954 | Nelson | 602/16 |
| 2,705,491 | 1/1955 | Hickerson | 602/16 |
| 3,295,517 | 1/1967 | Stevens . | |
| 4,543,948 | 10/1985 | Phillips | 602/23 |
| 4,697,808 | 10/1987 | Larson | 607/49 |
| 4,964,628 | 10/1990 | Poplawski . | |
| 4,969,452 | 11/1990 | Petrofsky | 602/16 X |

FOREIGN PATENT DOCUMENTS 9-173398  7/1997  Japan .
9-253145  9/1997  Japan .

OTHER PUBLICATIONS

The Journal of the International Society for Prosthetics and Orthotics, Dec. 1997, vol. 21, No. 3, pp. 222–228.

Primary Examiner—Richard J. Apley
Assistant Examiner—William LaMarca
Attorney, Agent, or Firm—Smith, Gambrell & Russell; Beveridge, DeGrandi, Weilacher & Young Intellectual Property Group

[57] ABSTRACT

An object of the present invention is to provide a walk assisting apparatus which enables persons having walking difficulties due to leg paralysis or other conditions to make the alternate walk improved for unassisted walking. The walk assisting apparatus according to the present invention comprises a left and a right full length leg brace swingably connected to left and right outer coxa links, an inner coxa link interconnecting the insides of the thighs of the left and the right leg supports, a swing center of the inner crotch link substantially coinciding with a swing center of the coxa links, so that the inner coxa link allows the leg supports to make the alternate walk properly.

8 Claims, 15 Drawing Sheets

WALK ASSISTING APPARATUS

BACKGROUND OF THE INVENTION

The present invention relates to a walk assisting apparatus which provides means for unassisted walking to a person having difficulty walking, such as from leg paralysis or other conditions.

The conventionally used walk assisting apparatus to be put on a person having difficulty walking who has sense paralysis or muscular function loss of both legs or the lower trunk due to damage to the medulla spinalis, is for a "large swing walk" in which the coxae are fixed, and both legs are simultaneously swung forward with the body weight born on crutches. However, this walk requires a wearer to consume very much energy, which makes it difficult for the wearer to walk long distances.

In view of this, walk assisting apparatuses which enable the "alternate walk," made by a normal person by alternately putting forward the left and the right legs, has been proposed. A problem with the conventional walk assisting apparatuses is that both leg supports have the same length, and when a wearer swings forward one leg, the sole of the leg is caught by the ground, which hinders the forward swing of the leg unless he much tilts the body. Accordingly, he is forced to walk forward, alternately tilting the body left and then right, which consumes his energy and destabilizes his walk.

A walk assisting apparatus has been proposed in which, by means of a gas pressure-type support length changing mechanism, a pair of the left and the right leg supports for fixing the legs of a wearer have support lengths extended and retracted in accordance with walking motions of the wearer so that one of the leg supports alternately becomes longer than the other. This walk assisting apparatus makes it necessary for a wearer to much tilt the body alternately left and right to walk, and makes it impossible for the wearer to stably make the alternate walk with relatively small energy consumption.

Here, in such alternate walk, when a wearer puts one of the legs forward, the other leg is left behind with respect to the body. The normal person unconsciously makes this motion. However, when a person having a walking difficulty makes the alternate walk, it is necessary that the legs are forcedly put forward alternately while the legs are interlocked with each other so that when one of the legs is put forward, the other is forcedly retreated.

An interlocking mechanism of full length walking braces for both legs of such walk assisting apparatus typically comprises, as exemplified in FIG. 15, interlocking shafts 109 mounted on rear parts of a trunk brace 102 by shafts and extended horizontally, and having a clutch 115 interposed between the interlocking shafts 109; first link members 101L, 101R having one end secured respectively to one end of the interlocking shafts 108 and extended in opposite direction to each other and normally to the interlocking shafts 109, and second link members 103L, 103R interconnecting the other ends of the first link members and leg supports 104L, 104R at points far below coxae 103L, 103R. The four-link mechanism constituted by the first and the second link members, the leg supports and the trunk brace 102 is interlocked by the interlocking shafts 109 so that when a wearer swings one leg forward, the other leg is retreated (see, e.g., Japanese Patent Laid-Open Publication No. 114089/1984).

However, the full length walking braces for both legs including such a conventional interlocking mechanism requires higher rigidity so that a person having difficulty walking can make the alternate walk motion as a normal person does. Higher rigidity adds weight to the brace, however, which gives a greater physical load to the person having difficulty walking.

As means for increasing the rigidity, a walk assisting apparatus includes full length walking braces for both legs which are mounted on a single shaft at an upper part inside the apparatus. However, in this walk assisting apparatus, the center of swing of the left and the right braces is positioned far remote from the physiological swing center of the coxae, which makes the normal alternate walk impossible. In the case where a trunk brace is necessary for a wearer having trouble in the upper spinal cord, an outside coxa link is provided, and the positions of the rotation axes of the inside shaft and of the outside link are much deflected from each other. As a result, a smooth walk is quite impossible, so that this type of walk assisting apparatus is applicable to restricted spinal cord damages.

SUMMARY OF THE INVENTION

The present invention is intended to remedy the above-described problems of the walk assisting apparatus for the alternate walk of leg-paralyzed persons. An object of the present invention is to provide a walk assisting apparatus in which an inner crotch link is rotated to thereby give a wearer of the apparatus a walking power sufficient to make stable walk, and, in addition, which can reduce the fall of an idling leg in an alternate walking motion.

The present invention is a walk assisting apparatus for solving the above-described object including left and right full length leg braces with a pelvis/trunk brace, and comprises the left and the right full length leg braces including a left and a right leg support connected below the left and the right lower ends of the pelvis/trunk brace to coxa links disposed at positions substantially corresponding to the coxae of a wearer, an inner crotch link interconnecting the insides of the left and the right thigh portions of the leg supports, a swing center of the inner crotch link substantially coinciding with a swing center of the coxa links, and the inner crotch link allowing the left and the right leg supports to make the alternate walk.

According to the walk assisting apparatus of the present invention, the inner crotch link interconnecting the leg supports is swung to give walking forces sufficient for a wearer to make stable walks, and can suppress variations in height of the center of gravity in the walk so as to improve the alternate walk. The trunk brace can be omitted to thereby facilitate wearing the apparatus and prevent physical loads to the wearer. The walk assisting apparatus according to the present invention can be used by persons having leg paralyses due to spinal cord damages, disabled persons having one leg, both thighs, or one or both legs below the coxa severed.

DETAILED DESCRIPTION OF THE PREFERRED EMBODIMENTS

A first embodiment of the present invention will be explained with reference to FIGS. 1 to 10.

Figure 1:
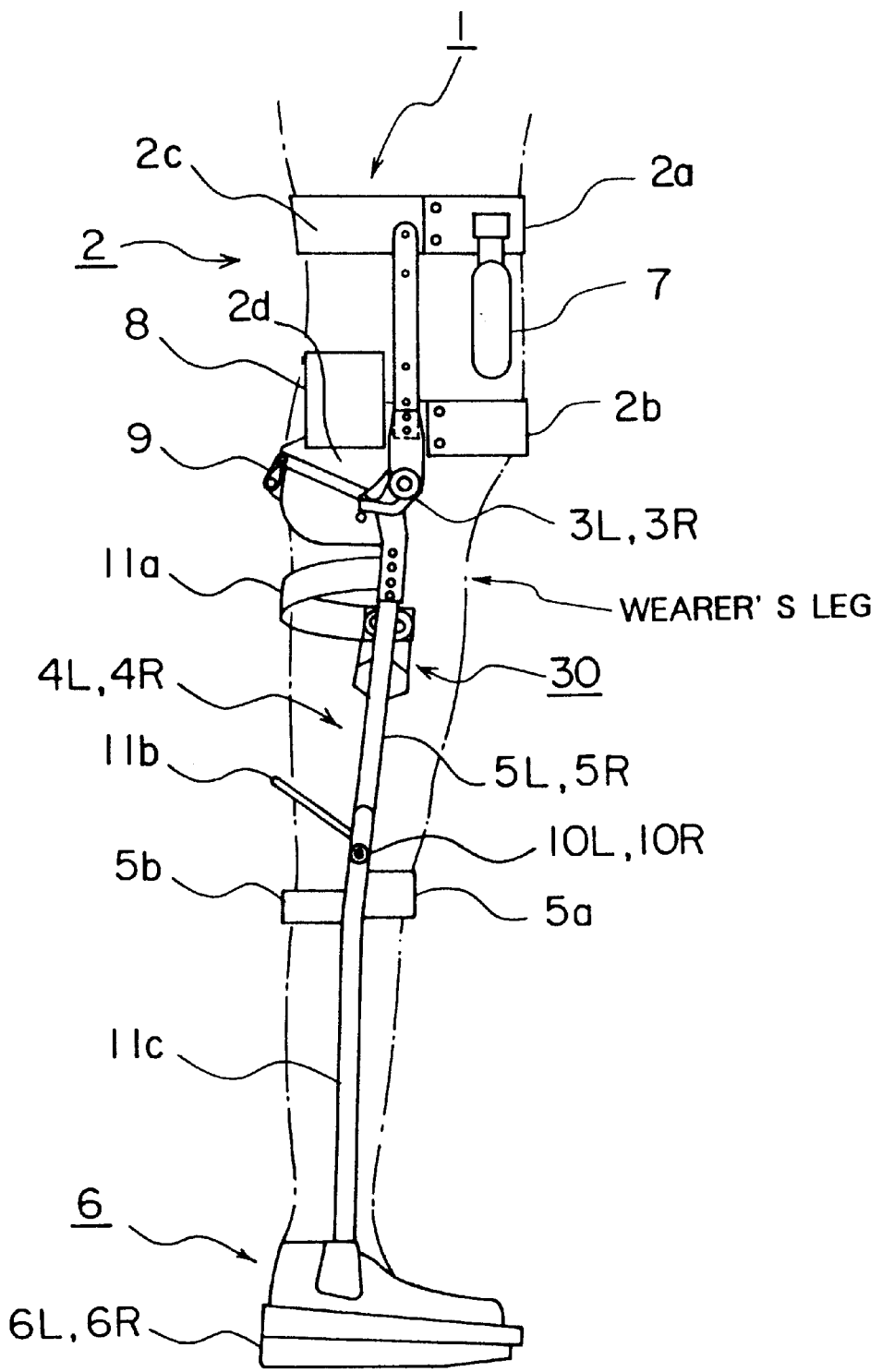
FIG. 1 is a side view of the walk assisting apparatus with a pelvis/trunk brace according to a first embodiment of the present invention, which shows a general structure thereof.
Figure 2:
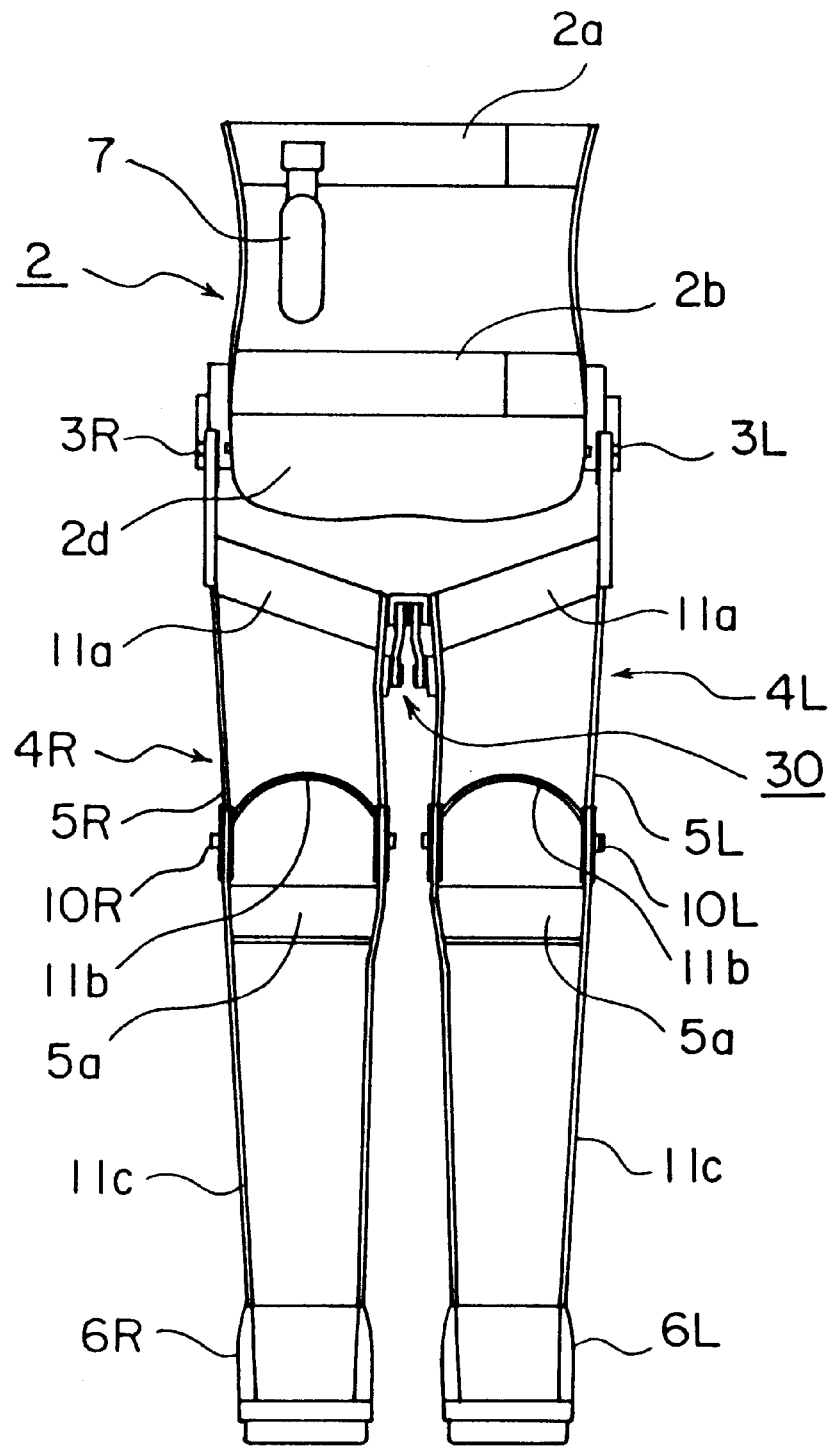
FIG. 2 is a front view of the walk assisting apparatus shown in FIG. 1.
Figure 3:
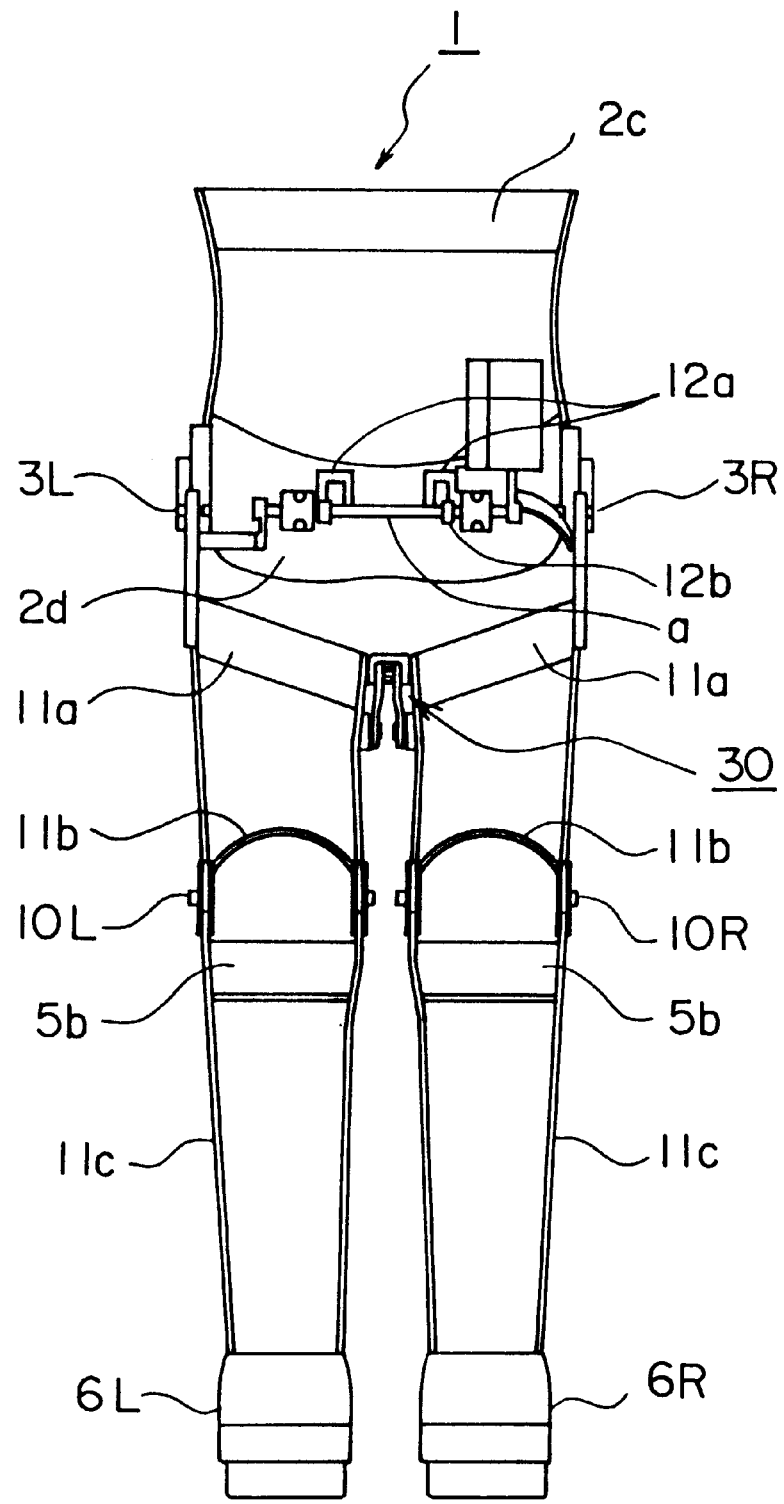
FIG. 3 is a back view of the walk assisting apparatus shown in FIG. 1.

As shown in FIGS. 1 to 3, in the walk assisting apparatus 1 according to a first embodiment of the present invention leg supports 5L, 5R, each for supporting the thigh and the shank of the leg of a wearer, are pivoted swingably forward and rearward in a walking direction on a pelvis/trunk brace 2 by left and right coxa links 3L, 3R provided on both sides of a pelvis/trunk brace 2. Foot mechanisms 6, 6 for supporting the feet of a wearer are attached to the lower ends of the leg supports 5L, 5R. Left and right full length leg braces 4L, 4R are constituted by the coxa links 3L, 3R, the leg supports 5L, 5R, brace supports 11C, 11C, knee-joint links 10L, 10R interconnecting the leg supports 5L, 5R and the brace supports 11C, 11C, knee lock release levers 11b, 11b connected to the knee-joint links 10L, 10R, and the foot mechanisms 6, 6. The leg supports 5L, 5R are connected to a reciprocation mechanism 9 through the coxa links 3L, 3R so as to be alternately swung in accordance with leg swing angles detected by angle sensors 12a, 12b.

Reference numerals 2a, 2b represent wearing belts of leather or others attached to the pelvis/trunk brace 2 for wearing the walk assisting apparatus. Reference numerals 2c, 2d indicate trunk supporting portions, and reference numerals 5a, 5b; 5a, 5b represent wearing belts and shank semicircular cuffs. The pelvis/trunk brace 2, the leg supports 5L, 5R and the feet mechanism 6 are mounted, by the aid of another person, on the trunk and the legs of a wearer from the back, and secured there by means of the wearing belts 2a, 5a, 5b, and the trunk support portions 2d, 2d.

The walk assisting apparatus 1 according to the first embodiment includes a leg support length changing mechanism (not shown) which alternately increases and decreases thicknesses of a left and a right feet 6L, 6R and heights of heels in accordance with a walking motion by controlling a $CO_2$ tank 7 mounted on the wearing belt 2a by operating control means by a wearer to feed $CO_2$ gas through a pipe (not shown) to the foot mechanism 6, 6.

The walk assisting apparatus 1 includes an inner crotch link 30.

As shown in FIGS. 2 and 3, the inner crotch link 30 interconnects the insides of the thigh portions of the left and the right leg supports 5L, 5R, and is disposed at a position where a swing center of the inner crotch joint 30 substantially coincides with a swing center of the coxa link 3L, 3R and physiological coxa centers of a wearer in an initial setting in the fabrication.

Figure 4:
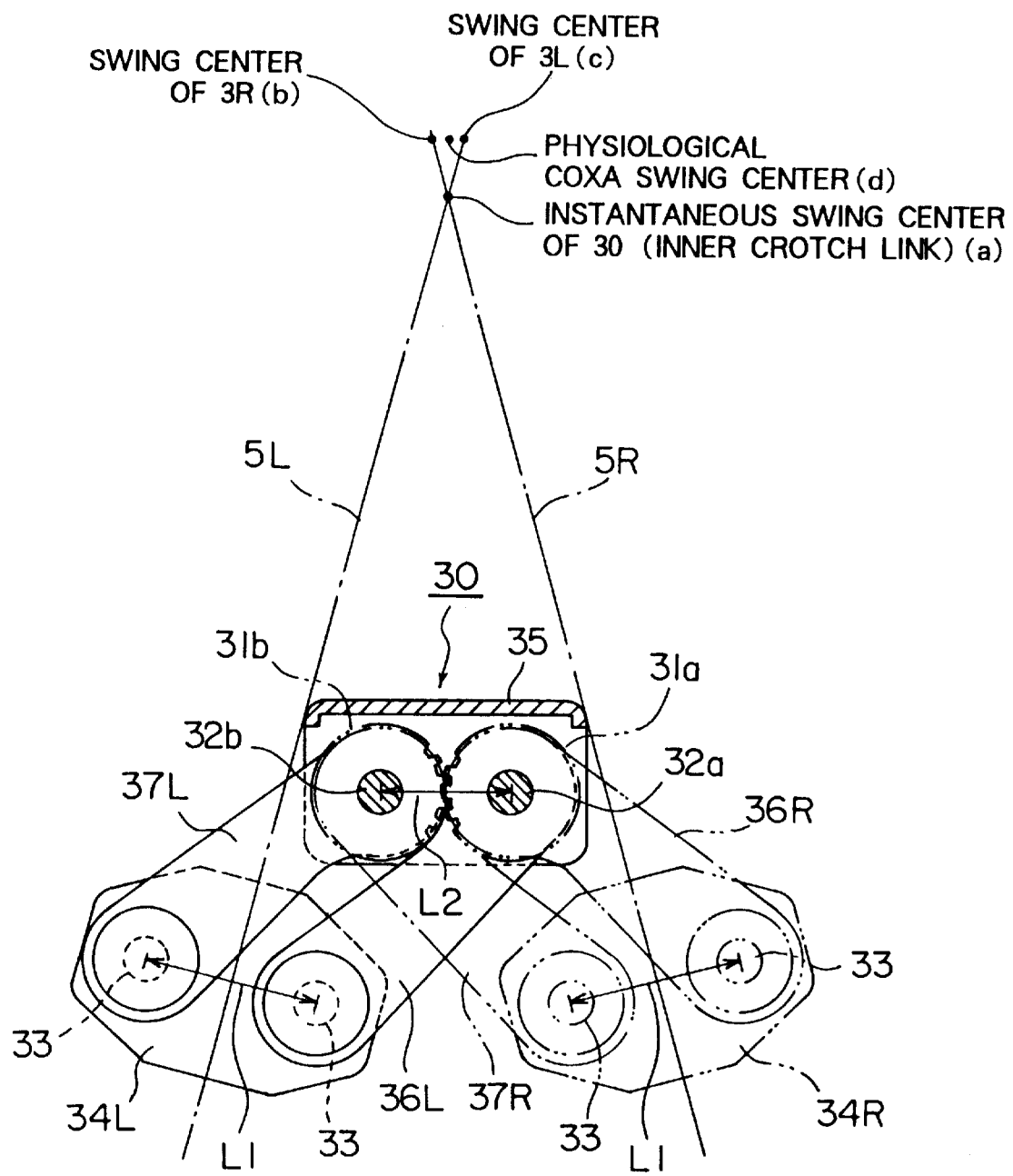
FIG. 4 is a partially broken side view (sectional view along the line III—III in FIG. 5) of an inner crotch link used in the walk assisting apparatus shown in FIG. 1.
Figure 5:
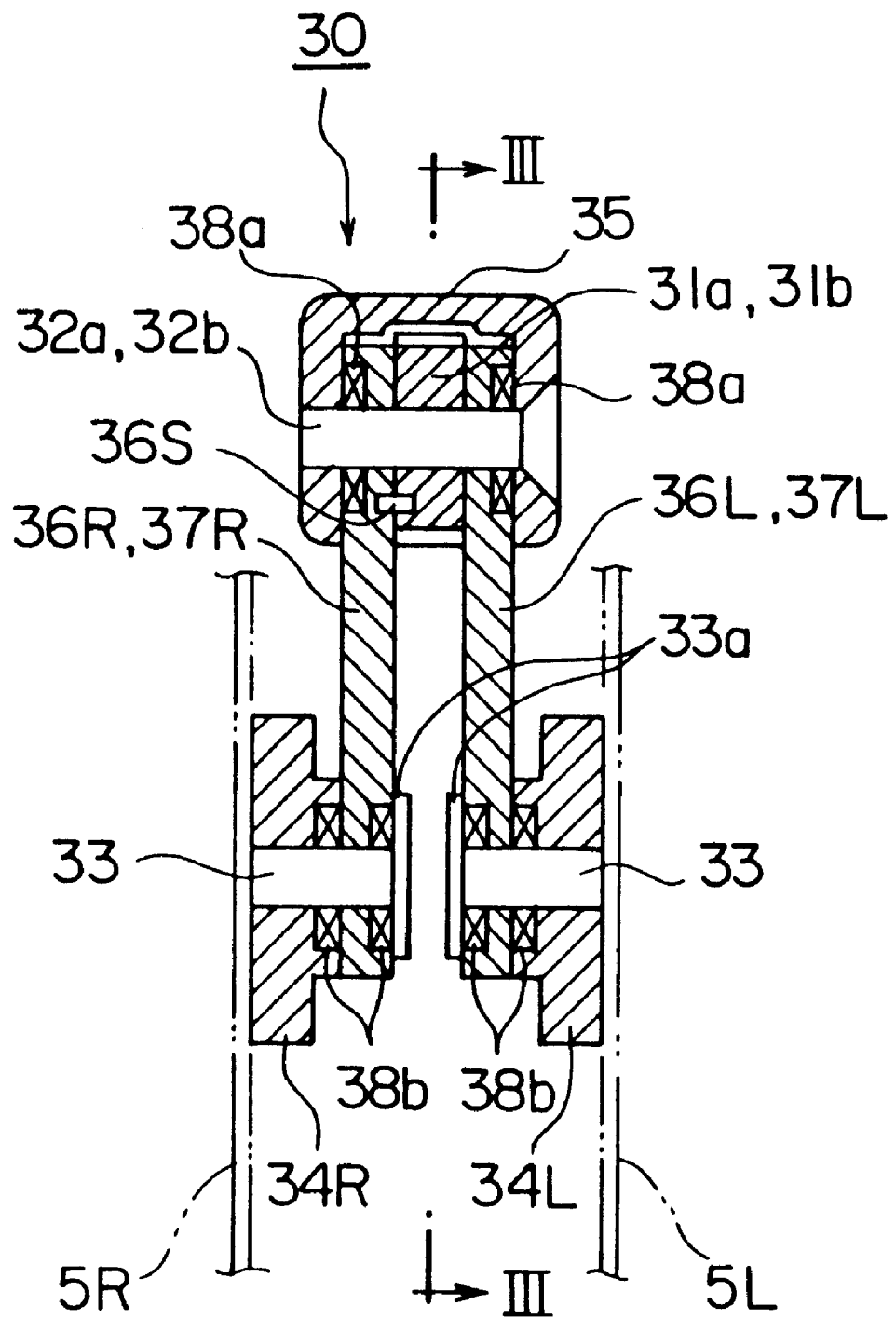
FIG. 5 is a vertical sectional view of the inner crotch link shown in FIG. 4.

As shown in FIGS. 4 and 5, the inner crotch joint 30 comprises a pair of synchronous pinion gears 31a, 31b disposed in a housing 35, mounted on a first shaft 32a and a second shaft 32b rotatably in directions opposite to each other, first and second link members 36L, 37L disposed substantially parallel with each other on the left and the right sides of the first pinion gear 31a, and first and second link members 36R, 37R disposed substantially parallel with each other on the left and the right sides of the second pinion gear 31b, and mounts 34L, 34R connected respectively to the lower ends of the first and the second link members 36L, 37L and to the lower ends of the first and the second link members 36R, 37R and fastened substantially normally to the leg supports 5L, 5R.

As detailed in FIG. 5, the upper ends of the first link members 36L, 36R and of the second link members 37L, 37R are mounted respectively on the first shaft 32a and the second shaft 32b. The upper end of the first link member 36R is integrated, by locking means 36S, with the synchronous pinion gear 31a on the right side of the synchronous pinion gear 31a, which is locked by the first shaft 32a. The upper end of the second link member 37R is not locked by the locking means and separated from the synchronous gear 31b on the right side thereof.

As detailed in FIG. 5, the upper end of the first link member 36L is not locked by the locking means and separated from the synchronous pinion gear 31a on the left side of the synchronous pinion gear 31a. The upper end of the second link member 37L is integrated, by the locking means 36S, with the synchronous pinion gear 31b on the left side of the synchronous pinion gear 31b.

The lower ends of the first link member 36L, 36R and of the second link members 37L, 37R are loosely mounted respectively on a pair of loose shafts 33, 33 in each of which (pairs) the loose shafts 33, 33 are spaced from each other by a prescribed lower inter-shaft distance L (see FIG. 6).

Thrust bearings 38a, 38a are provided between inside surfaces of the housing 35, and end surfaces of the first link members 36L, 36R and the second link members 37L, 37R. Thrust bearings 38b, 38b are provided also between the head surfaces 33a, 33a of the loose shafts 33, 33 and inside surfaces of the mounts 34L, 34R, and end surfaces of the first link members 36L, 36R and the second link members 37L, 37R. These thrust bearings 38a, 38b smooth swing of the link members with respect to the associated members.

When the leg supports 5L, 5R are positioned respectively forward and rearward in a walking direction as shown in FIG. 4, the inner crotch link 30 operates so that the first link and the second link member 36L, 37L disposed on the leg support 5L, and the mount 34L, and the first and second members 36R, 37R disposed on the second link member 37R, and the mount 34R are directed oppositely to each other. At this time, an upper inter-shaft distance L2 and a lower inter-shaft distance L1 between the first link members 36 and the second link members 37 are not varied.

In the walk assisting apparatus according to the above-described first embodiment of the present invention, when one leg support (e.g., the leg support 5R on the right side) is swung on the coxa joint 3R by a wearer when he walks, the mount 34R of the inner crotch joint 30 is swung forward, and the first link member 36R swings the first shaft 32a counter-clockwise and the synchronous pinion gear 31a counter-clockwise. The swing of the synchronous pinion gear 31a rotates the synchronous pinion gear 31b clockwise, and the second link member 37L on the left side is oppositely swung rearward on the second shaft 32b. Further, the second link member 37R follows the forward swing of the mount 34R to swing loosely on the second shaft 32b counter-clockwise. The opposite swing of the second link member 37L is accompanied by rearward swing of the mount 34L of the leg support 4L on the left side, and the first link member 36L on the left side follows the rearward swing of the mount 34L to loosely swing on the first shaft 32a clockwise.

Thus, in the inner crotch link 30, an inter-shaft distance L2, and a lower inter-shaft distance L1 of the mounts 34L, 34R, the first link members 36L, 36R and the second link members 37L, 37R constitute four-joint mechanisms on the left and the right sides of the synchronous pinion gears 31a, 31b.

The above-described left and right four-joint mechanisms swing the left and the right leg supports 5L, 5R in phases opposite to each other without failure in accordance with motions of the legs of a wearer so that the left and the right leg supports 5L, 5R are moved alternately through a pair of the synchronous pinion gears 31a.

Thus, when the leg supports 5L, 5R of the walk assisting apparatus 1 are alternately operated, a walking force of a wearer can be transmitted to the leg supports 5L, 5R at large torques generated with the axial centers of the coxa joints 3L, 3R as the centers. Accordingly, stable walk can be made.

According to the first embodiment, variation in height of the center of gravity of walks made by the alternate operation of the leg supports 5L, 5R can be suppressed to a minimum, whereby the alternate walk can be improved.

Next, with reference to FIG. 6A to FIG. 6E (as viewed on a side of the walk assisting apparatus), the operations of the leg supports 5L, 5R and the inner crotch joint 30 of the walk assisting apparatus 1 according to the first embodiment will be explained. In FIG. 6A to FIG. 6E, the walk assisting apparatus 1 is diagramed by straight lines and does not exactly agree with the actual configuration.

Figures 6A, 6B, 6C, 6D, 6E:
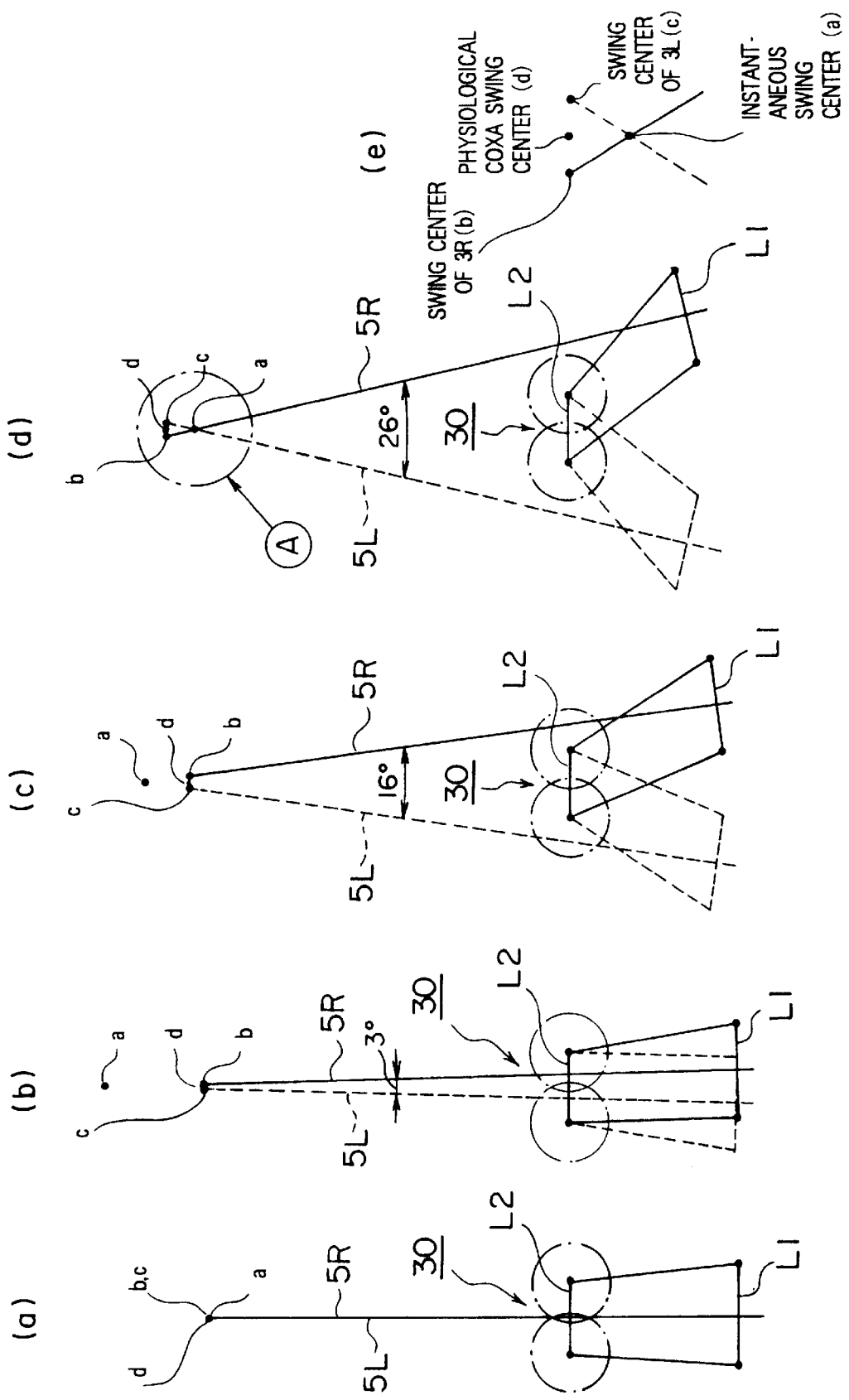
FIGS. 6A to FIG. 6D are explanatory views of the operation of the walk assisting apparatus shown in FIG. 1 as viewed on a side and FIG. 6E is a partial enlargement of part A in FIG. 6D.

FIG. 6A shows a state in which the left and the right leg supports 5L, 5R coincide in position with each other. Accordingly, the four joint mechanisms on the left and right sides of the inner crotch joint 20 coincide with each other in position. That is, this state is the initial setting in the fabrication of the walk assisting apparatus. In this state, the coxa links 3L, 3R coincide with the center(d) of the physiological coxae of a wearer in position. In this state, the angle difference of the inner crotch link 30, and the angle difference between the left and the right leg supports 5L, 5R is zero, and the angle between the left and the right legs of the wearer is zero.

FIG. 6B shows a state in which the left and the right leg supports 5L, 5R are swung by 3°. In this state, the four joint mechanisms on the left and the right side of the inner crotch link 30 are deformed in accordance with the motion of the leg supports and in opposite phases to each other.

FIG. 6C shows a state in which the left and the right leg support 5L, 5R are swung by 16°.

FIG. 6D shows a state in which the left and the right leg supports 5L, 5R are swung by 26°, which is a maximum value.

FIG. 6E shows a partially enlarged view of the part (A) in FIG. 6D.

Thus, it is clearly shown that the four joint mechanism of the inner crotch link 30 has an upper inter-shaft distance L2 as a fixed joint and is deformed on the fixed joint.

Regardless of the support leg angles (3°, 6°, 26°), as shown in FIGS. 6A to 6D, the swing center (d) of the physiological coxae of a wearer is located substantially at the middle of swing centers (b, c) of the left and the right coxa links 3L, 3R. In the walk assisting apparatus 1 in actual use, the positions of the physiological coxae of a wearer are considerably swung because of soft tissues, such as muscles, fat layers, etc. between the walk assisting apparatus and the skeleton of the wearer. A difference between actual positions of the coxae and a set position of the inner crotch link in the fabrication is 20 mm or more before and after the set position.

As shown in FIGS. 6A to 6D, an instantaneous swing center(a) of the inner crotch link 30 does not perfectly agree with a center (b, c) of the coxa links 3L, 3R disposed on the outsides thereof. When a support leg angle is varied as shown, an instantaneous swing center(a) of the inner crotch link 30 is vertically moved. Vertical errors due to these vertical movements are compensated for by some millimeter-resilient deformation of the walk assisting apparatus so that no practical inconvenience occurs.

A second embodiment of the present invention will be explained with reference to FIGS. 7 and 8.

Figure 7:
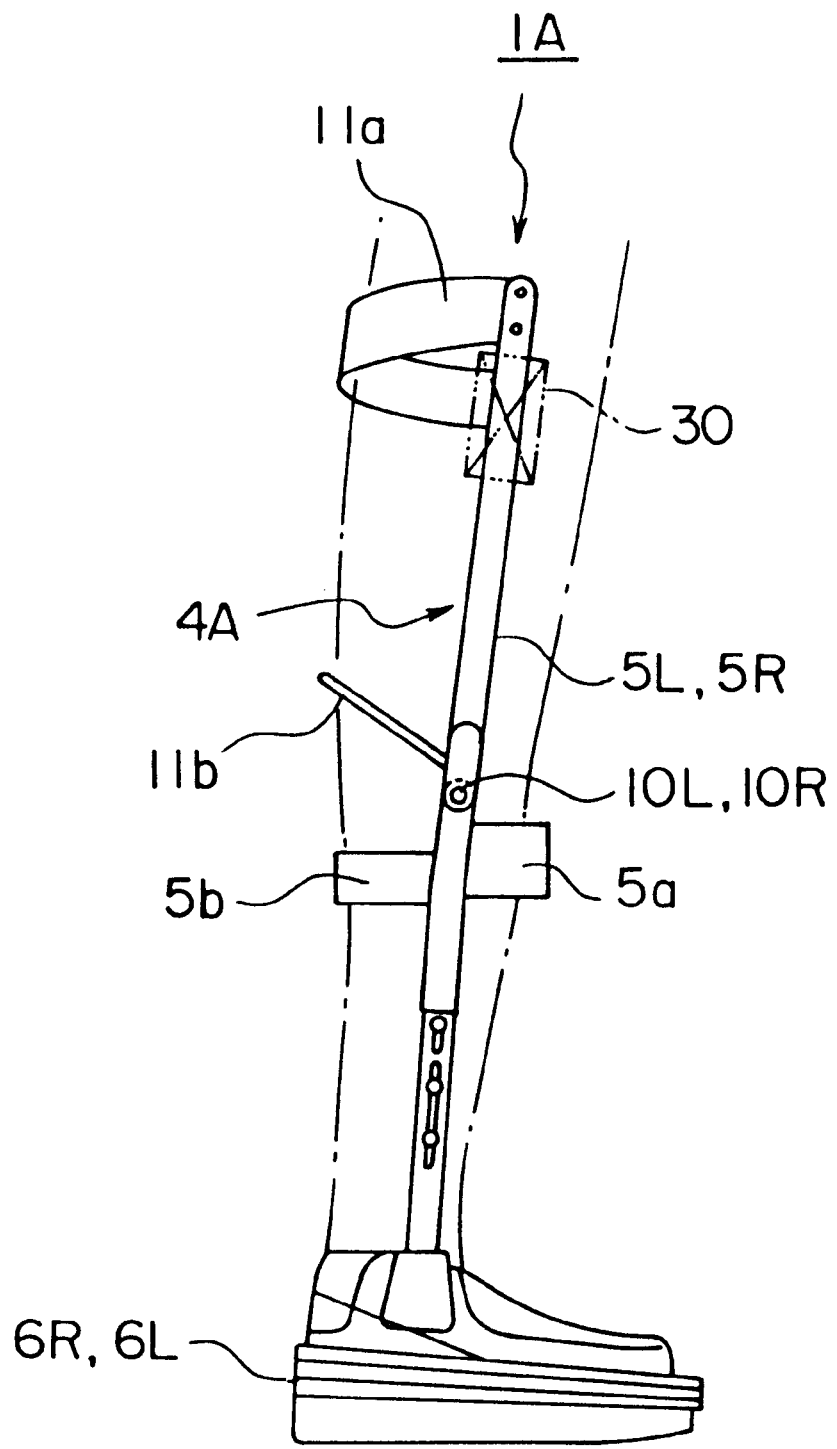
FIG. 7 is a side view of the walk assisting apparatus according to a second embodiment of the present invention, including full length leg braces, which explains the general structure thereof.
Figure 8:
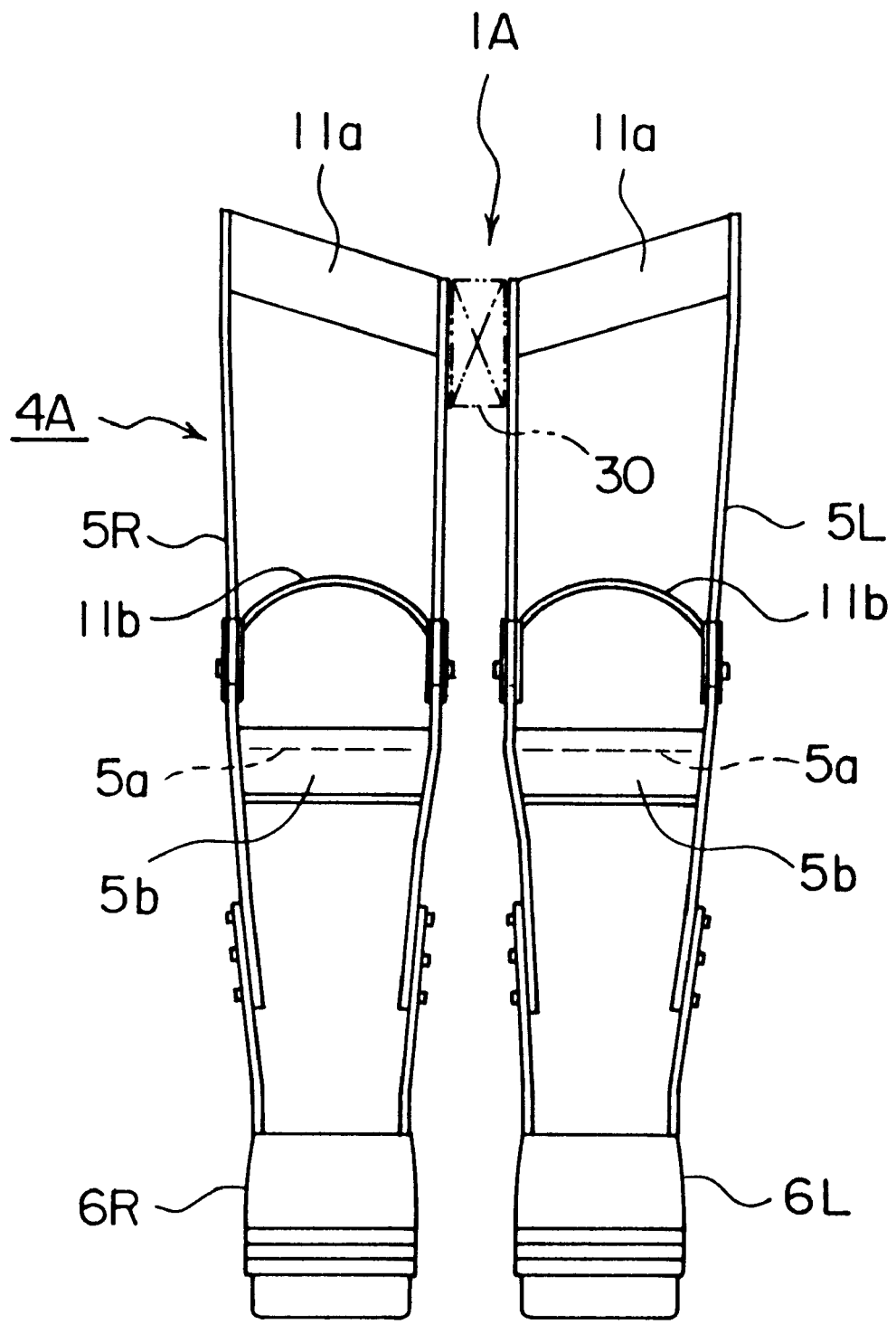
FIG. 8 is a front view of the walk assisting apparatus shown in FIG. 7.

As shown in FIGS. 7 and 8, the walk assisting apparatus 1A according to the second embodiment comprises both a full length leg brace 4A and an inner crotch link 30.

As in the first embodiment, the inner crotch link 30 interconnects the insides of the thigh portions of the left and the right leg supports 5L, 5R. A swing center of the inner crotch link 30 substantially coincides in position with the swing center of the physiological coxae of a person having a walking difficulty (wearer).

The walk assisting apparatus 1A according to the second embodiment is applicable to a person having a walking difficulty whose spinal cord damage is at a low part, e.g., a part between the thorax and the lumbar.

The walk assisting apparatus 1A according to the second embodiment has the structure of the assisting apparatus according to the first embodiment, but having the pelvis/trunk brace 2 omitted.

Accordingly, the walk assisting apparatus 1A according to the second embodiment can have an accordingly compact structure for moving the left and the right leg supports 5L, 5R to make the alternate walk. Furthermore, the walk assisting apparatus 1A according to the second embodiment can have a reduced weight, which makes it easy to take on and off the apparatus and resultantly can much reduce the physical load of persons having walking difficulties.

Next, a walk assisting apparatus according to a third embodiment of the present invention including another example of the inner crotch link will be explained with reference to FIGS. 9 and 10.

Figure 9:
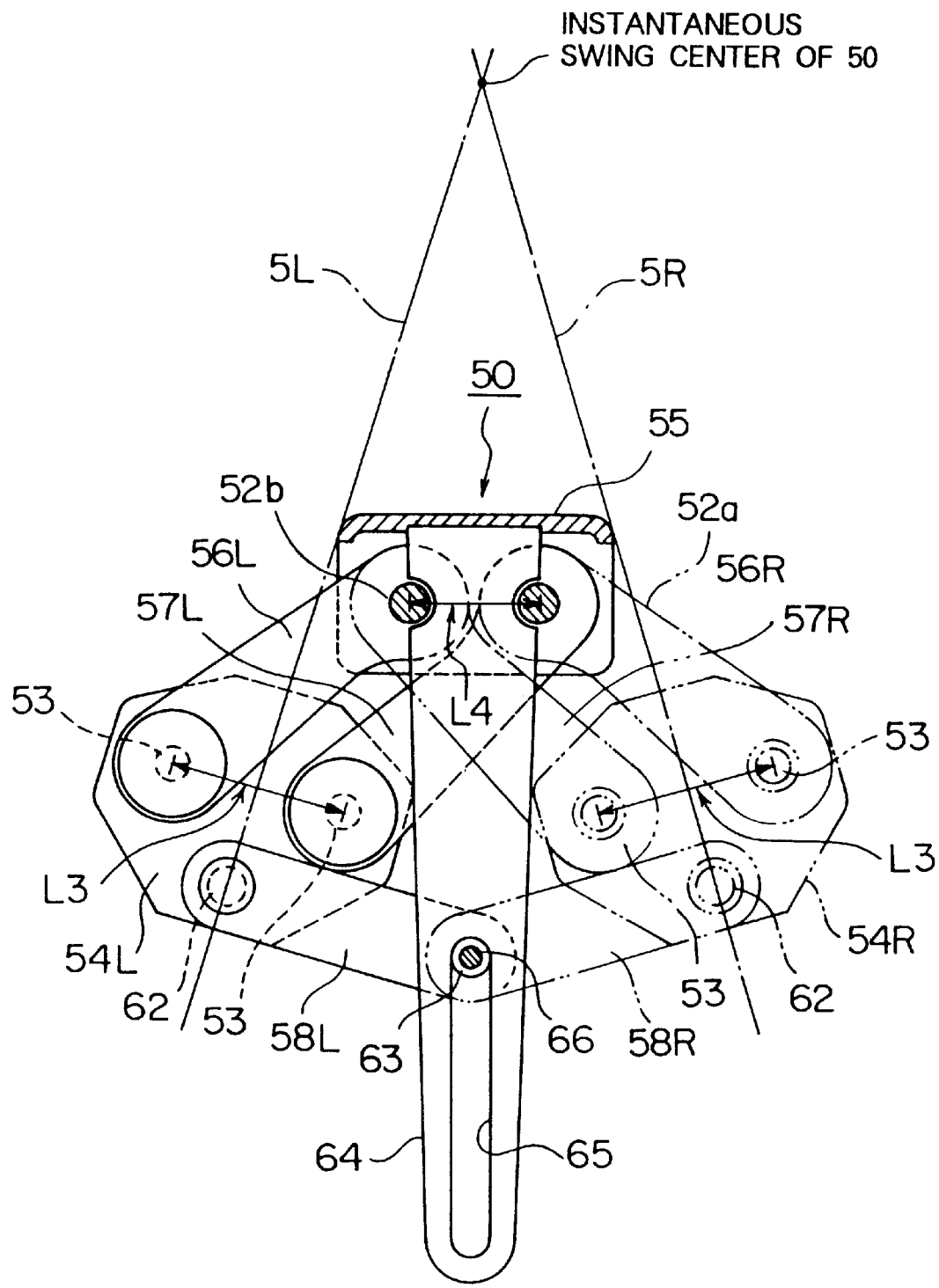
FIG. 9 is a partially broken sectional view (sectional view along the line VIII—VIII in FIG. 10) of the walk assisting apparatus according to a third embodiment of the present invention, which includes another example of the inner crotch link used in the walk assisting apparatus according to the first embodiment shown in FIG. 1.
Figure 10:
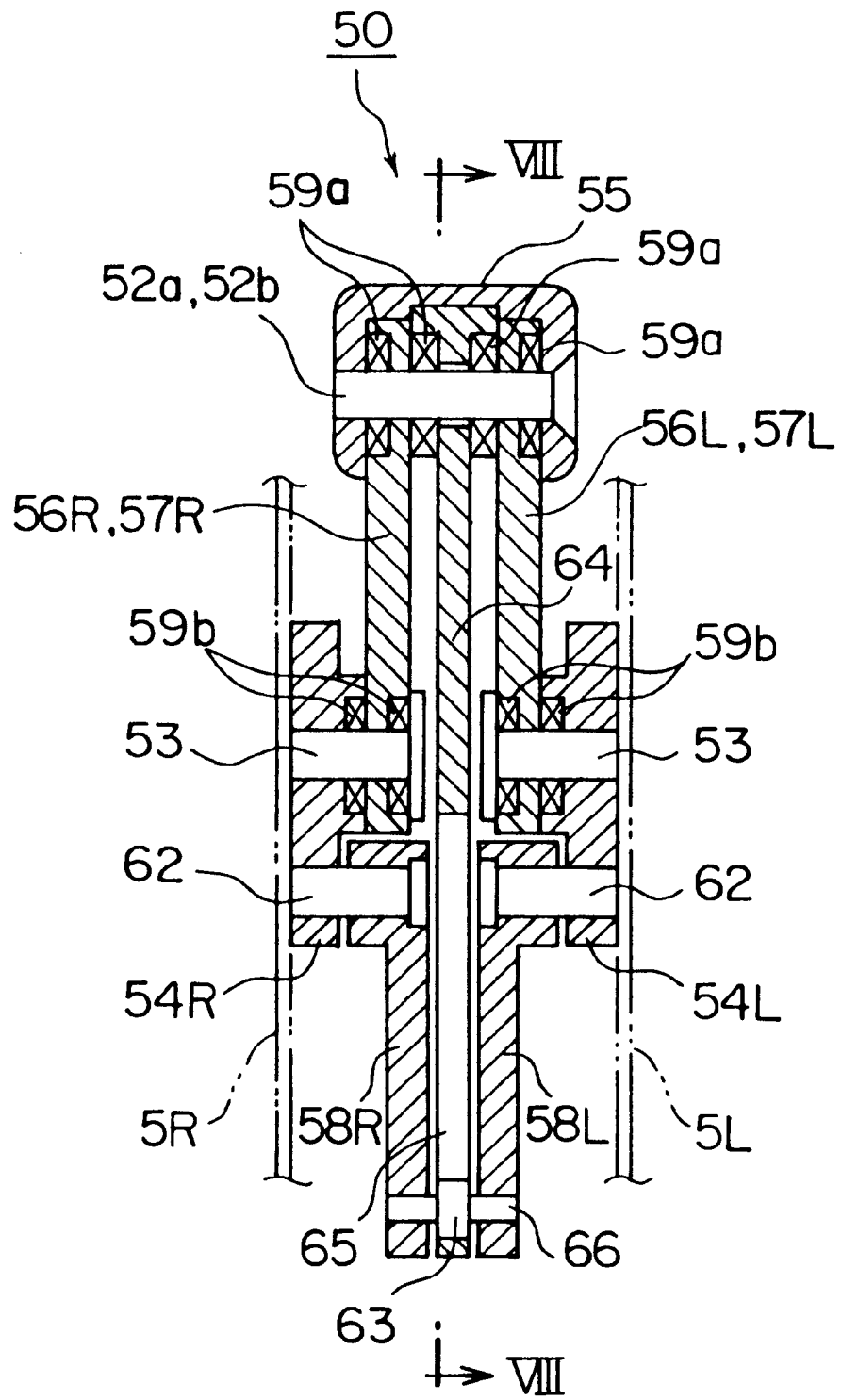
FIG. 10 is a vertical sectional view of the inner crotch link shown in FIG. 9.

As shown in FIGS. 9 and 10, in the third embodiment, the inner crotch link 50 comprises a guide member 64 extended vertically and mounted on the centers of a first shaft 52a and a second shaft 52b which are fixed shafts disposed in a housing 55, first link members 56L, 56R and second link members 57L, 57R respectively disposed parallel with each other on both sides of the guided member 64, a mount 54L to which the lower ends of the first link member 56L and the second link member 57L are fastened, and a mount 54R to which the lower ends of the first link member 56R and the second link member 57R are fastened to, and third link members 58L, 58R respectively interconnecting one side of the mounts 54L, 54R and the guide member 64.

The upper ends of the first link members 56L, 56R and the second link members 57L, 57R are loosely mounted respectively on the first shaft 52a, 52b. The lower ends of the first and the second link members 56L, 57R, and of the first and the second link members 58L, 58R are loosely connected respectively to the mounts 54L, 54R by first loose shafts 53, 53; 53, 53 respectively spaced from each other by a prescribed lower inter-shaft distance L3.

Thrust bearings 59a, 59a are interposed between inside surfaces of the housing 55, and surfaces of the first link members 36L, 36R and the second link members 37L, 37R. Thrust bearings 59b, 59b are interposed also between both side surfaces of the guide member 64, and the other surfaces of the first link members 56L and 56R and the second link members 57L and 57R. Furthermore, thrust bearings 59, 59 are interposed between the head surfaces of the loose shafts 53, 53 and inside surfaces of the mounts 54L, 56R, and both surfaces of the first link members 56L, 56R and the second link members 57L, 57R. Thus, swing of the link members is made smooth.

The third link members 58L, 58R each have one end loosely mounted on third loose shafts 62, 62 disposed on the mounts 54L, 54R near one side thereof and have the other ends loosely mounted on a roller shaft 66 on which a roller 63 is mounted. The guide member 54 has a slot-shaped guide groove 65 formed in a lower part thereof. The roller 63 is slid vertically in the guide groove 65.

In the inner crotch link 50, said inter-shaft distance L4, lower inter-shaft distances L3 on the respective mounts 61, the first link members 56L, 56R, and the second link members 57L, 57R constitute four-link mechanisms each on both sides of the fixed shaft 52a, 52b. Additionally, the third link members 58L, 58R, and the guide member 64 constitute two-joint mechanisms. Six-joint mechanisms are constituted as a whole.

In accordance with the above-described motions of a wearer's legs, the link members are alternately swung without failure in opposite phases to each other through the left and the right four-joint mechanisms and the two-joint mechanisms so as to alternately move the left and the right legs 5L, 5R.

The third embodiment omits the synchronous pinion gears used in the other above-described embodiments, whereby the inner crotch link 50 can be smoothly operated, and the inner crotch link 50 can be simplified as a whole.

The walk assisting apparatus according to a fourth embodiment of the present invention which includes another example of the crotch link mechanism will be explained with reference to FIGS. 11 to 13.

Figure 11:
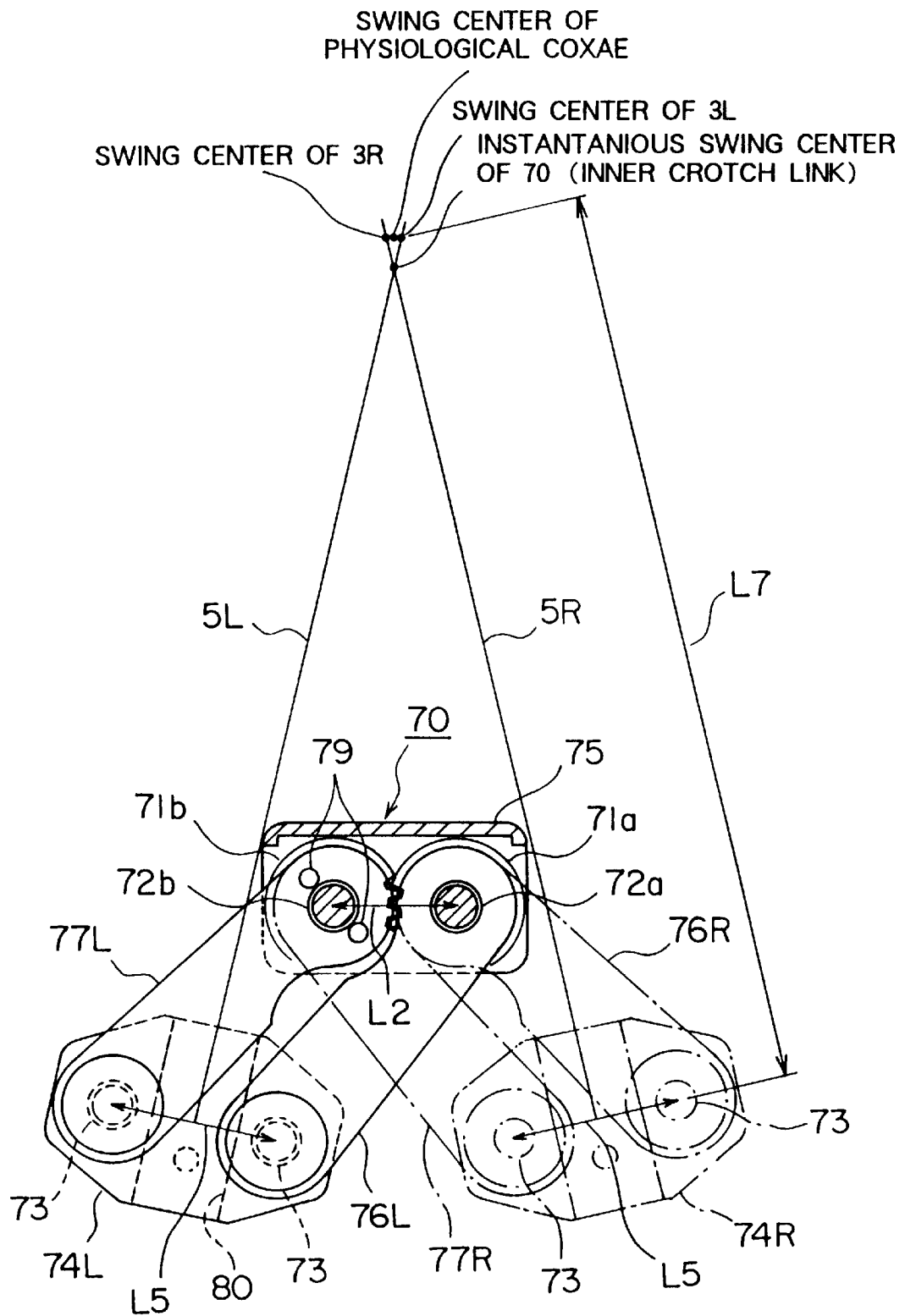
FIG. 11 is a partially broken sectional view (sectional view along the line X—X in FIG. 12) of the walk assisting apparatus according to a third embodiment of the present invention, which includes a further example of the inner crotch link used in the walk assisting apparatus according to the first embodiment shown in FIG. 1.
Figure 12:
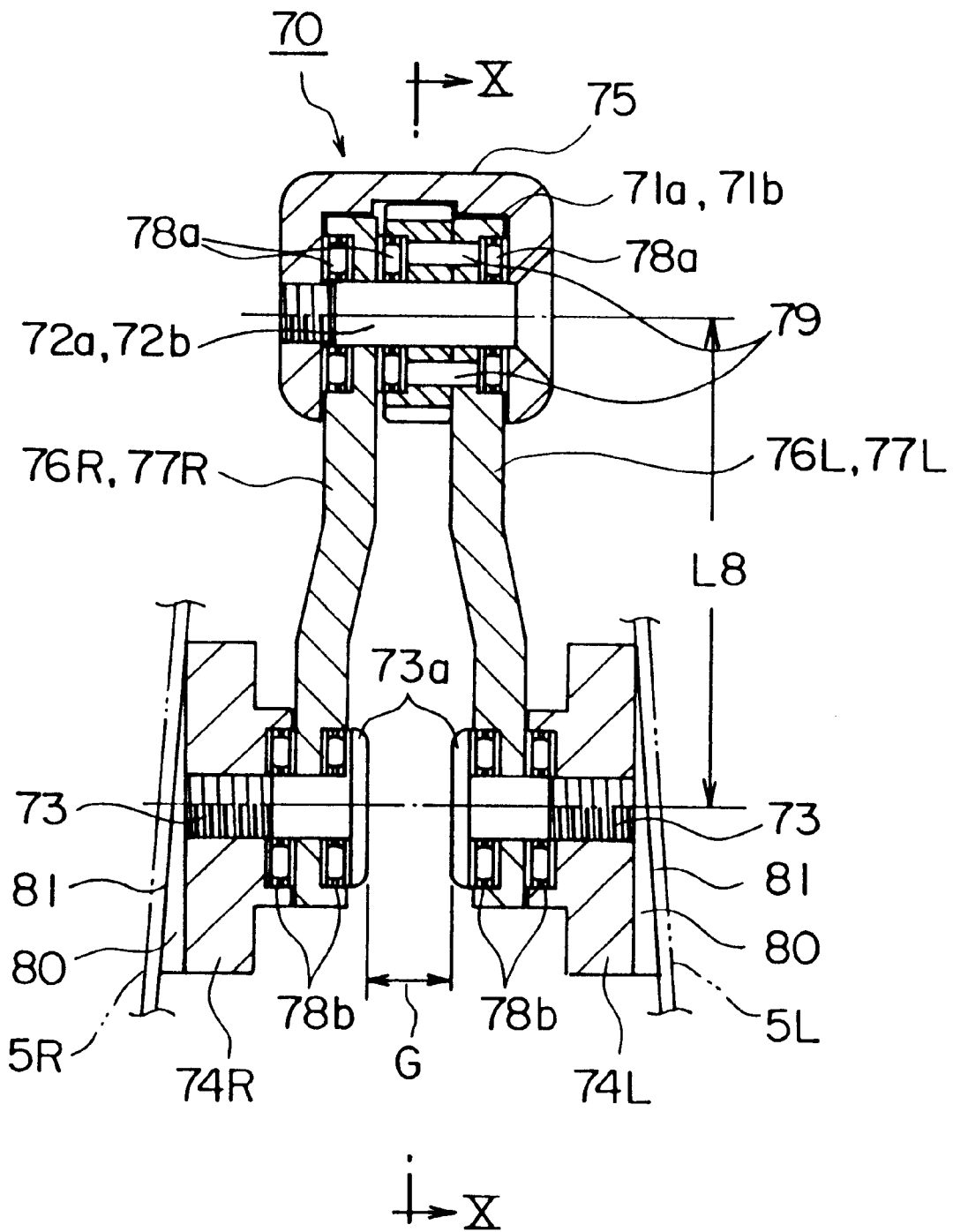
FIG. 12 is a vertical sectional view of the inner crotch link shown in FIG. 11.
Figure 13:
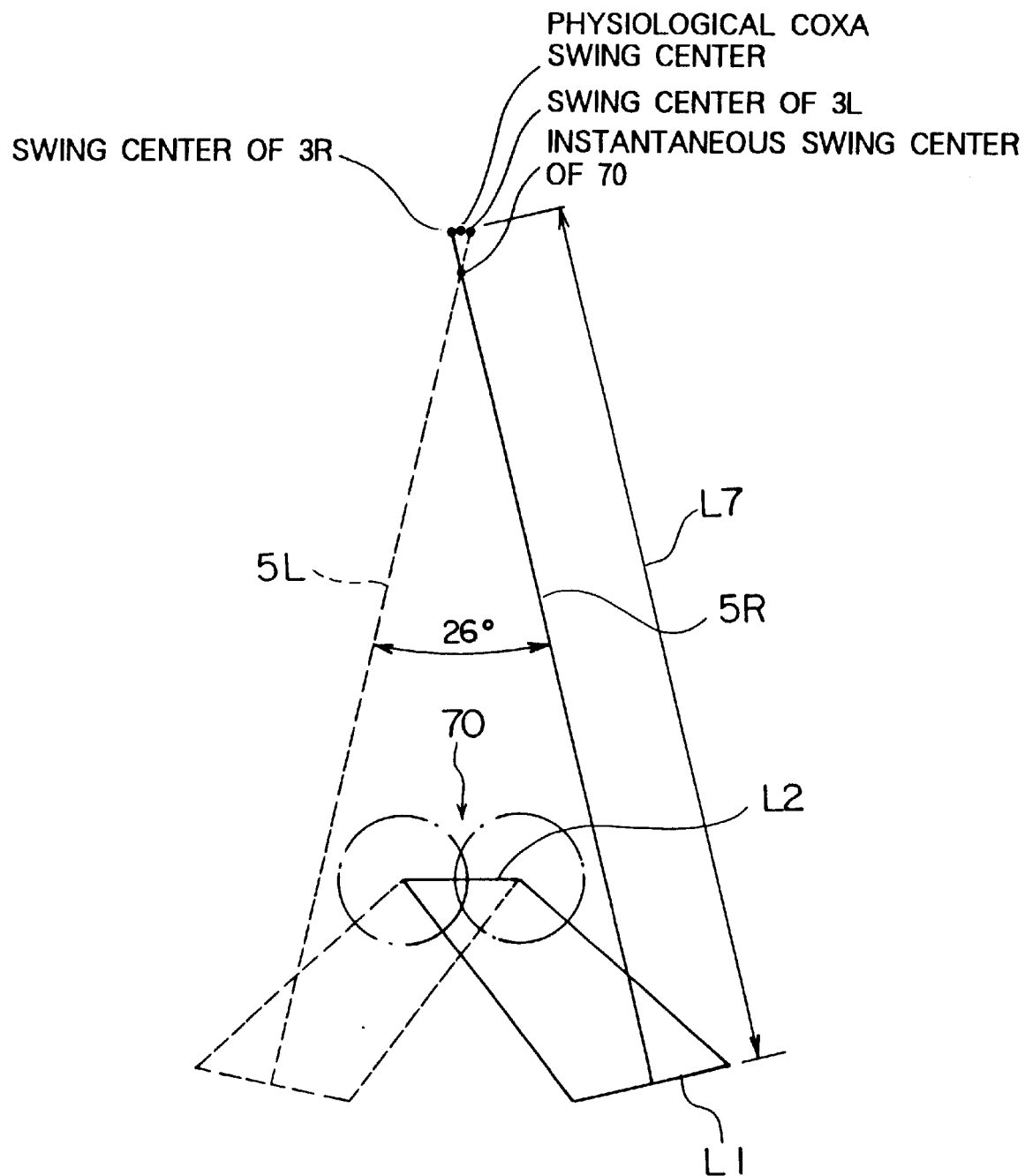
FIG. 13 is a side view of the walk assisting apparatus shown in FIG. 11, which explains the operation thereof.

As shown in FIGS. 11 and 12, in the walk assisting apparatus according to the fourth embodiment of the present invention, an inner crotch link 70 interconnects, as in the first embodiment, insides of the left and the right thigh portions of a left leg support 5L and a right leg support 5R. An instantaneous swing center of the inner crotch link 70 substantially coincides in time with the swing center of the physiological coxae of a wearer.

As shown in FIGS. 11 and 12, the inner crotch link 70 comprises a pair of synchronous pinion gears 71a, 71a mounted on a first shaft 72a and a second shaft 72b disposed in a housing 75 and swung in directions opposite to each other, first link members 76L, 76R and second link members 77L, 77R disposed substantially parallel with each other on the left and the right sides of the pinion gears 71a, 71b, and a mount 74L to which the lower ends of the first link member 76L and the second link member 77L are fastened to and a mount 74R to which the lower ends of the first link member 76R and the second link member 77R are fastened to.

As detailed in FIG. 12, the upper ends of the first link members 76L, 76R and of the second link members 77L, 77R are mounted respectively on the first shaft 72a and the second shaft 72b. The upper end of the first link member 76R is integrated with the synchronous pinion gear 71a by locking means 79 on the right side of the pinion gear 71a. The upper end of the second link member 77R is not locked by the locking means and separated from the synchronous pinion gear 71b on the right side of the pinion gear 71b.

The lower ends of the first link members 76L, 76R and of the second link members 77L, 77R are loosely mounted respectively on a pair of loose shafts 73, 73 which are spaced respectively from each other by a prescribed lower inter-shaft distance L5 (see FIG. 11).

As shown in FIG. 12, thrust bearings 78a, 78a are interposed between both inside surfaces of the housing 75, and end surfaces of the first link members 76L, 76R and the second link members 77L, 77R. Thrust bearings 78, 78 are interposed also between left surfaces of the synchronous pinion gears 71a, 71b, and right end surfaces of the first link members 76L, 76R.

Thrust bearings 78b, 78b are interposed also between the head surfaces 73a, 73a of the loose shaft 73, 73 and inside surfaces of the mounts 74L, 74R, and both end surfaces of the first link members 76L, 76R and the second link members 77L, 77R. Thus, swing of the link members is smoothed.

In the inner crotch link 70 of the fourth embodiment, as shown in FIG. 12, a longitudinal sectional shape of the first link members 76L, 76R and the second link members 77L, 77R are diverged form the first shaft 72a and the second shaft 72b toward the loose shafts 73, 73, so that a gap G formed between the head surfaces of the loose shafts 73, 73, i.e., a lower gap between the first and the second link members on the left and the right sides 76L, 76R, 77L, 77R, can be increased, for example, from 4 mm, which is the conventional lower gap, to 10 mm.

Thus in the fourth embodiment, a lower gap G between the first and the second link members 76L, 76R, 77L, 77R can be larger than lower gaps G of the other embodiments, where even when a person having a walking difficulty wears the walk assisting apparatus, he can wear clothes, such as pants or others, on the apparatus 1. The walk assisting apparatus 1 can thus be worn even by a person having a walking difficulty who is very conscious of appearance.

In the inner crotch link 70 of the present embodiment, as shown in FIG. 12, an inter-shaft gap L8 between the first and the second link members 76L, 76R, 77L, 77R, and the loose shafts 73, 73 can be increased, for example, from 55 mm, which is a conventional inter-shaft gap, to 60mm, and an error between the swing center of the physiological coxae, and that of the coxa links 3L, 3R of the apparatus is decreased. An inter-shaft distance (distance between the swing centers) between the coxa links 3L, 3R and the loose shafts 73, 73 can be increased, for example, from 170 mm, which is that of the other embodiments, to 190 mm, by moving a swing center of the inner crotch link 70 downward, whereby the inner crotch link 70 and the full length leg braces do not structurally interfere with each other, which facilities the fabrication of the apparatus as a whole.

Figure 14:
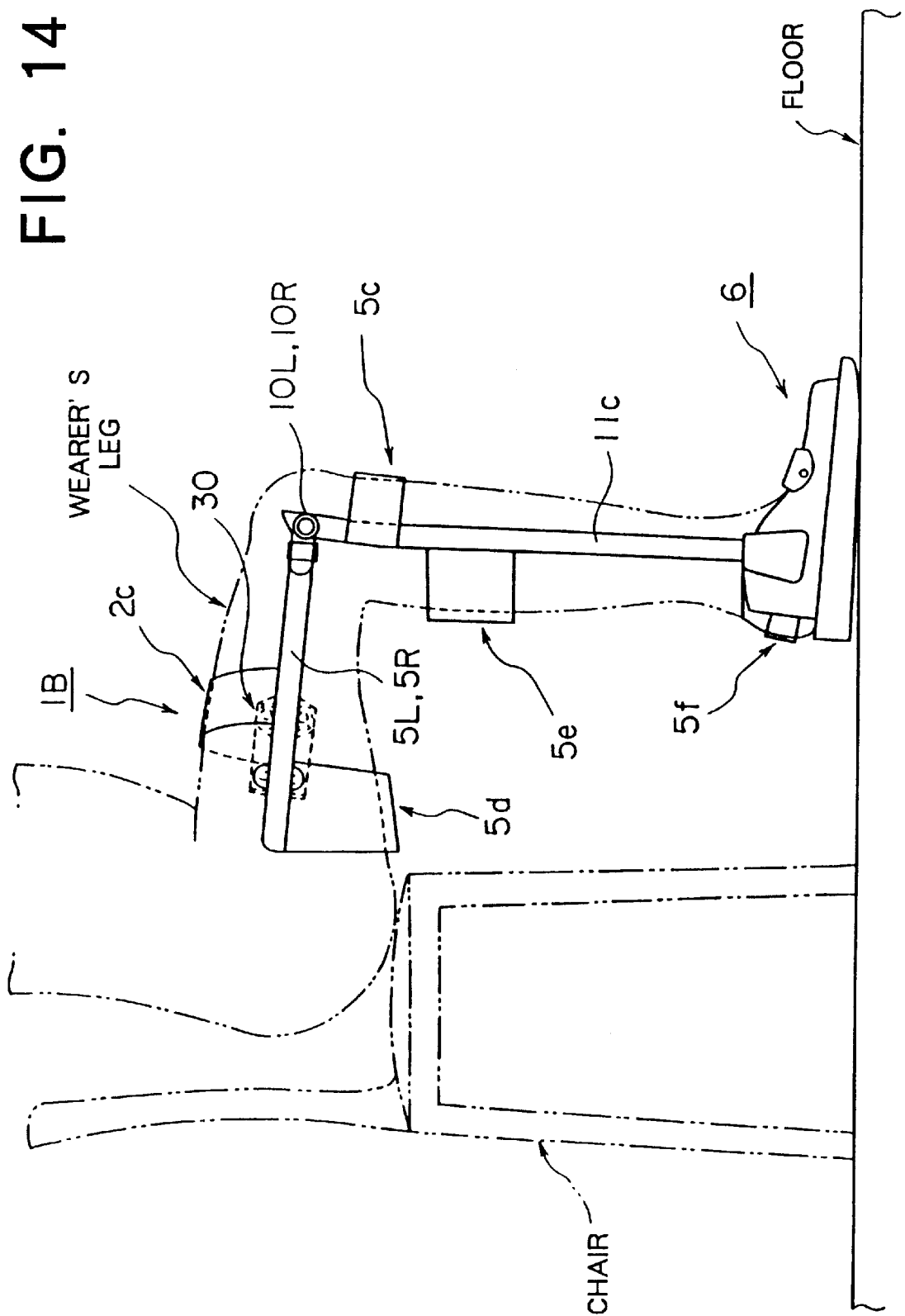
FIG. 14 is a side view of a modification of the walk assisting apparatus shown in FIG. 7.
Figure 15:
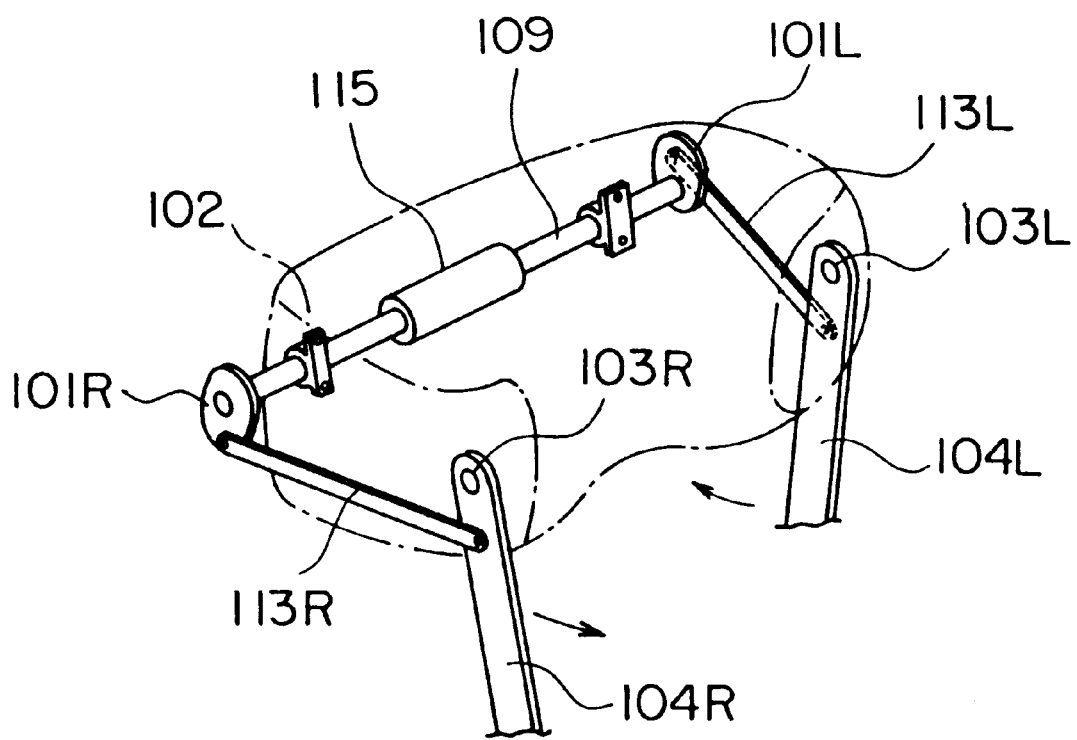
FIG. 15 is a perspective view of an interlocking mechanism for conventional full length leg braces.

As a modification of the walk assisting apparatus shown in FIGS. 7 and 8, a walk assisting apparatus 1B as shown in FIG. 14 which can be put on a wearer sitting on a chair from the front can be provided. The walk assisting apparatus 1B can be secured on the legs and feet of a wearer by means of a metal semicircular cuff 2C and wearing belts 5d, 5e, 5f which are soft belts. In place of the knee lock release lever, ring lock-type knee lock mechanisms are provided on knee joint links 10L, 10R.

What is claimed is:

1. A walk assisting apparatus comprising:
   a pelvis/trunk brace having a left and a right side, and having lower end portions on the left side and on the right side of the brace;
   full length leg braces including
      coxa links disposed on the lower end portions of the left and the right sides of the pelvis/trunk brace, which correspond to the coxa of a wearer, and
      left and right leg supports having left and right thigh portions; and
   an inner crotch link interconnecting insides of the left and the right thigh portions of the leg supports, the inner crotch link having a pivot axis and defining a crotch link swing center positioned above said pivot axis that substantially coincides with a swing center of the coxa links, whereby the inner crotch link moves the left and the right leg supports in an alternating fashion.

2. A walk assisting apparatus comprising:
   full length leg braces, including left and right leg supports each having a thigh portion;
   an inner crotch link interconnecting insides of the left and the right thigh portions of the leg supports, the inner crotch link having a pivot axis and defining a crotch link swing center that is positioned above said pivot axis and substantially coincides with a swing center of a position corresponding to the coxa of a wearer, whereby the inner crotch link move the left and right leg supports in an alternating fashion.

3. A walk assisting apparatus comprising:
   a pelvis/trunk brace having a left side and a right side, and having lower end portions on the left side and on the right side of the brace;
   full length leg braces including
      coxa links disposed on the lower end portions of the left and the right sides of the pelvis/trunk brace, which correspond to the coxa of a wearer, and
      left and right leg supports having left and right thigh portions; and
   an inner crotch link interconnecting insides of the left and the right thigh portions of the leg supports wherein a swing center of the inner crotch link substantially coincides with a swing center of the coxa links, whereby the inner crotch link can alternately move the left and the right leg supports, the inner crotch link further comprising:
      a housing;
      a pair of synchronous pinion gears mounted on fixed shafts locked to the housing, the pinion gears being rotatable in directions opposite to each other;
      first link members and second link members, each having two ends, a divergent shape, and being respectively disposed on a left and a right side of the respective pinion gears, one end of each of the first and second link members mounted respectively on the fixed shafts;
      loose shafts disposed on one side of mounts having two ends, on which mounts the other ends of the first link members and the second link members are loosely mounted, the other ends of the mounts being fastened to insides of the left and the right support legs normally to the support legs; wherein
   the synchronous pinion gears, the first link members, the second link members and the mounts move the left and the right support legs in opposite phases to each other so as to make leg alternate walk, whereby an inner gap between the left and the right support legs and a swing radius of the coxa links are maximum.

4. A walk assisting apparatus comprising:
   full length leg braces, including left and right leg supports each having a thigh portion;
   an inner crotch link interconnecting insides of the left and the right thigh portions of the leg supports wherein a swing center of the inner crotch link substantially coincides with a swing center of a position corresponding to the coxa of a wearer, whereby the inner crotch link can alternately move the left and the right leg supports, the inner crotch link further comprising:
      a housing;
      a pair of synchronous pinion gears mounted on fixed shafts locked to the housing, the pinion gears being rotatable in directions opposite to each other;
      first link members and second link members, each having two ends, a divergent shape, and being respectively disposed on a left and a right side of the respective pinion gears, one end of each of the first and second link members mounted respectively on the fixed shafts;
      loose shafts disposed on one side of mounts having two ends, on which mounts the other ends of the first link members and the second link members are loosely mounted, the other ends of the mounts being fastened to insides of the left and the right support legs normally to the support legs;
   the synchronous pinion gears, the first link members, the second link members and the mounts move the left and the right support legs in opposite phases to each other so as to make leg alternate walk, whereby an inner gap between the left and the right support legs and a swing radius of the coxa links are maximum.

5. The walk assisting apparatus according to claim 1, wherein the inner crotch link comprises:
   a housing;
   a pair of synchronous pinion gears mounted on fixed shafts fixed to the housing, the pinion gears being rotatable in directions opposite to each other;
   first link members and second link members, each having two ends, a divergent shape, and being respectively disposed on a left and a right side of the respective pinion gears, one end of each of the first and second link members mounted respectively on the fixed shafts;
   loose shafts disposed on one side of mounts having two ends, on which mounts the other ends of the first link members and the second link members are rotatively mounted, the other side of the mounts being fastened to insides of the left and the right support legs normally to the support legs; wherein the synchronous pinion gears, the first link members, the second link members and the mounts move the left and the right support legs in opposite phases to each other so as to move the right and the left leg supports in the alternating fashion.

6. The walk assisting apparatus according to claim 2, wherein the inner crotch link comprises:

a housing;

a pair of synchronous pinion gears mounted on fixed shafts fixed to the housing, the pinion gears being rotatable in directions opposite to each other;

first link members and second link members, each having two ends, a divergent shape, and being respectively disposed on a left and a right side of the respective pinion gears, one end of each of the first and second link members mounted respectively on the fixed shafts;

loose shafts disposed on one side of mounts having two ends, on which mounts the other ends of the first link members and the second link members are rotatively mounted, the other side of the mounts being fastened to insides of the left and the right support legs normally to the support legs; wherein the synchronous pinion gears, the first link members, the second link members and the mounts move the left and the right support legs in opposite phases to each other so as to move the right and the left leg supports in the alternating fashion.

7. The walk assisting apparatus according to claim 1, wherein the inner crotch link comprises:

a housing;

a guide member, mounted on fixed shafts fixed to the inside of the housing and extending vertically therefrom, first link members and second link members disposed respectively on the left and the right sides of the guide member, first ends of the first link members and second link members being rotatively mounted respectively on the fixed shafts;

first loose shafts and second loose shafts, positioned on mounts, to which the second ends of the first link members and the second ends of the second link members respectively are rotatively mounted;

third link members, disposed on the left and the rights sides of the guide member, and interconnecting the guide member and one side of the mounts below the first link members and the second link members; and a roller, on which one end of the third link members are rotatively mounted, the roller being slidable in a straight guide groove formed in the guide member, the other side of the mounts being fastened to insides of the left and the right leg supports normally to the leg supports, whereby the first link members, the second link members, the third link members, the guide member and the mounts move the left and the right leg supports in opposite phases to each other so as to move the left and the right leg supports in the alternating fashion.

8. The walk assisting apparatus according to claim 2, wherein the inner crotch link comprises:

a housing;

a guide member, mounted on fixed shafts fixed to the inside of the housing and extending vertically therefrom;

first link members and second link members disposed respectively on the left and the right sides of the guide member, first ends of the first link members and second link members being rotatively mounted respectively on the fixed shafts;

first loose shafts and second loose shafts, positioned on mounts, to which the second ends of the first link members and the second ends of the second link members respectively are rotatively mounted;

third link members, disposed on the left and the rights sides of the guide member, and interconnecting the guide member and one side of the mounts below the first link members and the second link members; and a roller, on which one end of the third link members are rotatively mounted, the roller being slidable in a straight guide groove formed in the guide member, the other side of the mounts being fastened to insides of the left and the right leg supports normally to the leg supports, whereby the first link members, the second link members, the third link members, the guide member and the mounts move the left and the right leg supports in opposite phases to each other so as to move the left and the right leg supports in the alternating fashion.

\* \* \* \* \*